(12) United States Patent
Alessi et al.

(10) Patent No.: US 9,682,127 B2
(45) Date of Patent: Jun. 20, 2017

(54) OSMOTIC DELIVERY DEVICE COMPRISING AN INSULINOTROPIC PEPTIDE AND USES THEREOF

(71) Applicant: Intarcia Therapeutics, Inc., Boston, MA (US)

(72) Inventors: Thomas R. Alessi, Hayward, CA (US); Ryan D. Mercer, Dublin, CA (US); Catherine M. Rohloff, Los Altos, CA (US); Bing Yang, Redwood City, CA (US)

(73) Assignee: INTARCIA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/291,523

(22) Filed: Oct. 12, 2016

(65) Prior Publication Data

US 2017/0072022 A1  Mar. 16, 2017

Related U.S. Application Data

(60) Continuation of application No. 14/605,348, filed on Jan. 26, 2015, now abandoned, which is a continuation of application No. 12/927,432, filed on Nov. 15, 2010, now Pat. No. 8,940,316, which is a division of application No. 12/148,896, filed on Apr. 22, 2008, now Pat. No. 8,299,025, which is a continuation-in-part of application No. 11/347,562, filed on Feb. 3, 2006, now Pat. No. 8,114,437.

(60) Provisional application No. 60/926,005, filed on Apr. 23, 2007, provisional application No. 61/072,202, filed on Mar. 28, 2008, provisional application No. 60/650,225, filed on Feb. 3, 2005.

(51) Int. Cl.

| | | |
|---|---|---|
| *A61K 38/26* | (2006.01) |
| *A61K 9/00* | (2006.01) |
| *A61K 9/10* | (2006.01) |
| *A61K 9/16* | (2006.01) |
| *A61K 9/70* | (2006.01) |
| *A61K 47/14* | (2017.01) |
| *C07K 7/06* | (2006.01) |
| *C07K 14/605* | (2006.01) |
| *A61K 47/12* | (2006.01) |
| *A61K 47/20* | (2006.01) |
| *A61K 47/26* | (2006.01) |
| *A61K 47/32* | (2006.01) |

(52) U.S. Cl.
CPC .......... *A61K 38/26* (2013.01); *A61K 9/0004* (2013.01); *A61K 9/0024* (2013.01); *A61K 9/10* (2013.01); *A61K 9/1617* (2013.01); *A61K 9/1623* (2013.01); *A61K 9/7023* (2013.01); *A61K 47/12* (2013.01); *A61K 47/14* (2013.01); *A61K 47/20* (2013.01); *A61K 47/26* (2013.01); *A61K 47/32* (2013.01); *C07K 7/067* (2013.01); *C07K 14/605* (2013.01); *Y10T 29/494* (2015.01)

(58) Field of Classification Search
CPC .............................. A61K 38/26; C07K 14/605
See application file for complete search history.

(56) References Cited

U.S. PATENT DOCUMENTS

| | | |
|---|---|---|
| 2,110,208 A | 3/1938 | Eggert |
| 2,168,437 A | 8/1939 | Buercklin |
| 3,025,991 A | 3/1962 | Gillon |
| 3,122,162 A | 2/1964 | Sands |
| 3,625,214 A | 12/1971 | Higuchi |
| 3,632,768 A | 1/1972 | Bergy et al. |
| 3,732,865 A | 5/1973 | Higuchi et al. |
| 3,797,492 A | 3/1974 | Place |
| 3,869,549 A | 3/1975 | Geller |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |
| 4,111,202 A | 9/1978 | Theeuwes |
| 4,111,203 A | 9/1978 | Theeuwes |
| 4,203,439 A | 5/1980 | Theeuwes |

(Continued)

FOREIGN PATENT DOCUMENTS

| | | |
|---|---|---|
| EP | 0079405 | 5/1983 |
| EP | 0254394 | 1/1988 |

(Continued)

OTHER PUBLICATIONS

"Abstracts 2007," Diabetologia Clinical & Experimental Diabetes & Metabolism, Springer, Berlin, Germany, vol. 50 S243 (Aug. 21, 2007) (paragraph [0586]) (XP002538652).

(Continued)

*Primary Examiner* — Gyan Chandra
(74) *Attorney, Agent, or Firm* — Coolep LLP; Ivor R. Elrifi

(57) ABSTRACT

A suspension formulation of an insulinotropic peptide (e.g., glucagon-like peptide-1 (GLP-1) or exenatide) is described. The suspension formulation comprises (i) a non-aqueous, single-phase vehicle, comprising one or more polymer and one or more one solvent, wherein the vehicle exhibits viscous fluid characteristics, and (ii) a particle formulation comprising the insulinotropic peptide, wherein the peptide is dispersed in the vehicle. The particle formulation further includes a stabilizing component comprising one or more stabilizers, for example, carbohydrates, antioxidants, amino acids, and buffers. Devices for delivering the suspension formulations and methods of use are also described.

30 Claims, 4 Drawing Sheets

(56) References Cited

U.S. PATENT DOCUMENTS

| | | |
|---|---|---|
| 4,211,771 A | 7/1980 | Witkowski et al. |
| 4,243,030 A | 1/1981 | Lynch et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher et al. |
| 4,439,196 A | 3/1984 | Higuchi |
| 4,455,143 A | 6/1984 | Theeuwes et al. |
| 4,455,145 A | 6/1984 | Theeuwes |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |
| 4,695,623 A | 9/1987 | Stabinsky |
| 4,727,138 A | 2/1988 | Goeddel et al. |
| 4,734,284 A | 3/1988 | Terada et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,820,638 A | 4/1989 | Swetly et al. |
| 4,826,144 A | 5/1989 | Balsells |
| 4,830,344 A | 5/1989 | Balsells |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,952,402 A | 8/1990 | Sparks et al. |
| 4,957,119 A | 9/1990 | de Nijs |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |
| 5,006,346 A | 4/1991 | Edgren et al. |
| 5,019,382 A | 5/1991 | Cummins, Jr. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,126,142 A | 6/1992 | Ayer et al. |
| 5,134,244 A | 7/1992 | Balsells |
| 5,137,727 A | 8/1992 | Eckenhoff |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Magruder et al. |
| 5,190,765 A | 3/1993 | Jao et al. |
| 5,203,849 A | 4/1993 | Balsells |
| 5,207,752 A | 5/1993 | Sorenson et al. |
| 5,209,746 A | 5/1993 | Balaban et al. |
| 5,213,809 A | 5/1993 | Wright et al. |
| 5,219,572 A | 6/1993 | Sivaramakrishnan |
| 5,221,278 A | 6/1993 | Linkwitz et al. |
| 5,223,265 A | 6/1993 | Wong |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| 5,278,151 A | 1/1994 | Korb et al. |
| 5,279,608 A | 1/1994 | Cherif Cheikh |
| 5,284,655 A | 2/1994 | Bogdansky et al. |
| 5,290,271 A | 3/1994 | Jernberg |
| 5,300,302 A | 4/1994 | Tachon et al. |
| 5,308,348 A | 5/1994 | Balaban et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magruder et al. |
| 5,324,280 A | 6/1994 | Wong et al. |
| 5,336,057 A | 8/1994 | Fukuda et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,429,602 A | 7/1995 | Hauser |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,543,156 A | 8/1996 | Roorda et al. |
| 5,545,618 A | 8/1996 | Buckley et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,595,751 A | 1/1997 | Bezwada |

(56) References Cited

U.S. PATENT DOCUMENTS

| | | |
|---|---|---|
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,633,011 A | 5/1997 | Dong et al. |
| 5,635,213 A | 6/1997 | Nystrom et al. |
| 5,639,477 A | 6/1997 | Maruyama et al. |
| 5,645,850 A | 7/1997 | Bezwada et al. |
| 5,648,088 A | 7/1997 | Bezwada et al. |
| 5,660,847 A | 8/1997 | Magruder et al. |
| 5,660,858 A | 8/1997 | Parikh et al. |
| 5,660,861 A | 8/1997 | Jao et al. |
| 5,668,170 A | 9/1997 | Gyory |
| 5,676,942 A | 10/1997 | Testa et al. |
| 5,686,097 A | 11/1997 | Taskovich et al. |
| 5,690,925 A | 11/1997 | Gray et al. |
| 5,690,952 A | 11/1997 | Magruder et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,711,967 A | 1/1998 | Juch |
| 5,713,847 A | 2/1998 | Howard, III et al. |
| 5,728,088 A | 3/1998 | Magruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Lorenz et al. |
| 5,782,396 A | 7/1998 | Mastri et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Magruder et al. |
| 5,874,388 A | 2/1999 | Hsu |
| 5,876,746 A | 3/1999 | Jona et al. |
| 5,882,676 A | 3/1999 | Lee et al. |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,948,430 A | 9/1999 | Zerbe et al. |
| 5,958,909 A | 9/1999 | Habener |
| 5,962,023 A | 10/1999 | Jamiolkowski et al. |
| 5,972,370 A | 10/1999 | Eckenhoff et al. |
| 5,972,373 A | 10/1999 | Yajima et al. |
| 5,976,109 A | 11/1999 | Heruth |
| 5,985,305 A | 11/1999 | Peery et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,029,361 A | 2/2000 | Newman |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,113,938 A | 9/2000 | Chen et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,191,102 B1 | 2/2001 | DiMarchi et al. |
| 6,204,022 B1 | 3/2001 | Johnson et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| 6,258,377 B1 | 7/2001 | New et al. |
| 6,261,584 B1 | 7/2001 | Peery et al. |
| 6,268,343 B1 | 7/2001 | Knudsen et al. |
| 6,270,787 B1 | 8/2001 | Ayer |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamiolkowski et al. |
| 6,524,305 B1 | 2/2003 | Peterson et al. |
| 6,528,486 B1 | 3/2003 | Larsen et al. |
| 6,541,021 B1 | 4/2003 | Johnson et al. |
| 6,544,252 B1 | 4/2003 | Theeuwes et al. |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,670,368 B1 | 12/2003 | Breault et al. |
| 6,673,767 B1 | 1/2004 | Brodbeck et al. |

(56) References Cited

U.S. PATENT DOCUMENTS

| | | |
|---|---|---|
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiewicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,902,744 B1 | 6/2005 | Kolterman et al. |
| 6,903,186 B1 | 6/2005 | Dong |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,612,176 B2 | 11/2009 | Wright et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 | 2/2011 | Alessi et al. |
| 7,919,109 B2 | 4/2011 | Berry et al. |
| 7,959,938 B2 | 6/2011 | Rohloff et al. |
| 7,964,183 B2 | 6/2011 | Eliaz et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,257,691 B2 | 9/2012 | Eliaz et al. |
| 8,263,545 B2 | 9/2012 | Levy et al. |
| 8,263,736 B2 | 9/2012 | Bloom |
| 8,268,341 B2 | 9/2012 | Berry |
| 8,273,365 B2 | 9/2012 | Lautenbach et al. |
| 8,273,713 B2 | 9/2012 | Pittner et al. |
| 8,278,267 B2 | 10/2012 | Weyer et al. |
| 8,288,338 B2 | 10/2012 | Young et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 | 8/2014 | Alessi et al. |
| 8,865,202 B2 | 10/2014 | Zerbe et al. |
| 8,926,595 B2 | 1/2015 | Alessi et al. |
| 8,940,316 B2 | 1/2015 | Alessi et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0031790 A1 | 10/2001 | Beisswenger et al. |
| 2001/0036472 A1 | 11/2001 | Wong et al. |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jaworowicz et al. |
| 2002/0048600 A1 | 4/2002 | Bhatt et al. |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 5/2003 | Jolly et al. |
| 2003/0104063 A1 | 6/2003 | Babcock et al. |
| 2003/0108608 A1 | 6/2003 | Laridon et al. |
| 2003/0108609 A1 | 6/2003 | Berry et al. |
| 2003/0113380 A1 | 6/2003 | Ramstack et al. |
| 2003/0118660 A1 | 6/2003 | Rickey et al. |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith |
| 2004/0001889 A1 | 1/2004 | Chen et al. |
| 2004/0002442 A1 | 1/2004 | Pan et al. |

(56) References Cited

U.S. PATENT DOCUMENTS

| | | |
|---|---|---|
| 2004/0022859 A1 | 2/2004 | Chen et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0053370 A1 | 3/2004 | Glaesner et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 8/2004 | Chen et al. |
| 2004/0151753 A1 | 8/2004 | Chen et al. |
| 2004/0198654 A1 | 10/2004 | Glaesner et al. |
| 2004/0209801 A1 | 10/2004 | Berry et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0070883 A1 | 3/2005 | Brown et al. |
| 2005/0079200 A1 | 4/2005 | Rathenow et al. |
| 2005/0079202 A1 | 4/2005 | Chen et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0084604 A1 | 4/2006 | Kitaura et al. |
| 2006/0094652 A1 | 5/2006 | Levy et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0247463 A1 | 10/2009 | Wright et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2011/0076317 A1 | 3/2011 | Alessi et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0034210 A1 | 2/2013 | Rohloff et al. |
| 2013/0052237 A1 | 2/2013 | Eliaz et al. |
| 2015/0111818 A1 | 4/2015 | Alessi et al. |
| 2015/0231062 A1 | 8/2015 | Lautenbach et al. |
| 2015/0231256 A1 | 8/2015 | Berry et al. |
| 2015/0297509 A1 | 10/2015 | Schwarz |
| 2016/0030337 A1 | 2/2016 | Kuzma et al. |

FOREIGN PATENT DOCUMENTS

| | | |
|---|---|---|
| EP | 0295411 | 12/1988 |
| EP | 0368339 | 5/1990 |
| EP | 0373867 | 6/1990 |
| EP | 0431942 | 6/1991 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2020990 | 9/2010 |
| FR | 640907 | 7/1928 |
| GB | 1049104 | 11/1966 |
| GB | 1518683 | 7/1978 |
| JP | 9241153 | 9/1997 |
| JP | 11-100353 | 4/1999 |
| JP | 2006/213727 A | 8/2006 |
| NZ | 592113 | 8/2012 |
| TW | 200634060 | 10/2006 |
| WO | WO 91/07160 | 5/1991 |
| WO | WO 93/06819 | 4/1993 |
| WO | WO 93/06821 | 4/1993 |
| WO | WO 93/08832 | 5/1993 |
| WO | WO 93/09763 | 5/1993 |
| WO | WO 93/23083 | 11/1993 |
| WO | WO 94/09743 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |

(56) References Cited

FOREIGN PATENT DOCUMENTS

| | | |
|---|---|---|
| WO | WO 95/34285 | 12/1995 |
| WO | WO 9601134 | 1/1996 |
| WO | WO 96/03116 | 2/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO 97/15289 | 5/1997 |
| WO | WO 97/15296 | 5/1997 |
| WO | WO 97/28181 | 8/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/27962 | 7/1998 |
| WO | WO 98/27963 | 7/1998 |
| WO | WO 98/30231 | 7/1998 |
| WO | WO 98/32463 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/04768 | 2/1999 |
| WO | WO 99/16419 | 4/1999 |
| WO | WO 99/25728 | 5/1999 |
| WO | WO 99/29306 | 6/1999 |
| WO | WO 99/33446 | 7/1999 |
| WO | WO 99/33449 | 7/1999 |
| WO | WO 99/39700 | 8/1999 |
| WO | WO 99/40788 | 8/1999 |
| WO | WO 99/44659 | 9/1999 |
| WO | WO 99/62501 | 12/1999 |
| WO | WO 99/64061 | 12/1999 |
| WO | WO 00/13663 | 3/2000 |
| WO | WO 00/29206 | 5/2000 |
| WO | WO 00/38652 | 7/2000 |
| WO | WO 00/39280 | 7/2000 |
| WO | WO 00/40273 | 7/2000 |
| WO | WO 00/41548 | 7/2000 |
| WO | WO 00/45790 | 8/2000 |
| WO | WO 00/54745 | 9/2000 |
| WO | WO 00/66138 | 11/2000 |
| WO | WO 00/67728 | 11/2000 |
| WO | WO 01/43528 | 6/2001 |
| WO | WO 01/51041 | 7/2001 |
| WO | WO 01/78683 | 10/2001 |
| WO | WO 02/28366 | 4/2002 |
| WO | WO 02/36072 | 5/2002 |
| WO | WO 02/43800 | 6/2002 |
| WO | WO 02/45752 | 6/2002 |
| WO | WO 02/47716 | 6/2002 |
| WO | WO 02/067895 | 9/2002 |
| WO | WO 02/069983 | 9/2002 |
| WO | WO 02/076344 | 10/2002 |
| WO | WO 02/085428 | 10/2002 |
| WO | WO 03/000230 | 1/2003 |
| WO | WO 03/007981 | 1/2003 |
| WO | WO 03/011892 | 2/2003 |
| WO | WO 03/024357 | 3/2003 |
| WO | WO 03/024503 | 3/2003 |
| WO | WO 03/030923 | 4/2003 |
| WO | WO 03/041684 | 5/2003 |
| WO | WO 03/041757 | 5/2003 |
| WO | WO 03/053400 | 7/2003 |
| WO | WO 03/072113 | 9/2003 |
| WO | WO 03/072133 | 9/2003 |
| WO | WO 2004/002565 | 1/2004 |
| WO | WO 2004/052336 | 6/2004 |
| WO | WO 2004/056338 | 7/2004 |
| WO | WO 2004/089335 | 10/2004 |
| WO | WO 2005/048930 | 6/2005 |
| WO | WO 2005/048952 | 6/2005 |
| WO | WO 2005/102293 | 11/2005 |
| WO | WO 2006/017772 | 2/2006 |
| WO | WO 2006/023526 | 3/2006 |
| WO | WO 2006/081279 | 8/2006 |
| WO | WO 2006/083761 | 8/2006 |
| WO | WO 2006/084139 | 8/2006 |
| WO | WO 2006/086727 | 8/2006 |
| WO | WO 2006/101815 | 9/2006 |
| WO | WO 2006/111169 | 10/2006 |
| WO | WO 2007/024700 | 3/2007 |
| WO | WO 2007/056681 | 5/2007 |
| WO | WO 2007/075534 | 7/2007 |
| WO | WO 2007/084460 | 7/2007 |
| WO | WO 2007/133778 | 11/2007 |
| WO | WO 2007/140416 | 12/2007 |
| WO | WO 2008/021133 | 2/2008 |
| WO | WO 2008/061355 | 5/2008 |
| WO | WO 2008/133908 | 11/2008 |
| WO | WO 2008/134425 | 11/2008 |
| WO | WO 2009/109927 | 9/2009 |

OTHER PUBLICATIONS

Jetschmann et al., "Open-label rising-dose study of omega interferon in IFN-naive patients with chronic hepatitis C," Gastroenterology 122:A278-A347 (Apr. 1, 2002) (Abstract M1454).

Bray, "Gut Signals and Energy Balance: Ghrelin, Peptide YY, Leptin, and Amylin," (Dec. 19, 2007) (slides and transcript for presentation at Medscape CME).

"Implantable infusion pumps: technology poised for takeoff," BBI Newsletter 17(12):209-211 (Dec. 1994).

Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).

Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).

Adolf et al., "Antigenic structure of human interferon ω1 (Interferon αII1): comparison with other human interferons," J. Gen. Virol. 68(6):1669-1676 (Jun. 1987).

Adolf et al., "Purification and characterization of natural human interferon ω1," J. Bio. Chem. 265(16):9290-9295 (Jun. 1990).

Adolf et al., "Human interferon ω1: isolation of the gene, expression in Chinese hamster ovary cells and characterization of the recombinant protein," Biochim. Biophys. Acta 108(9):167-174 (Jun. 1991).

Andrx Pharmaceuticals, LLC, Anda for Concerta® Extended-Release Tablets, 6 pages (correspondence dated Sep. 6, 2005).

ASTM International, Annual Book of ASTM Standards, 8.02:208-211, 584-587 (1984).

Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).

Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).

Aulitzky, " Successful Treatment of Metastatic Renal Cell Carcinoma With a Biologically Active Dose of Recombinant Interferon-Gama," Journal of Clinical Oncology 7(12):1875-1884 (1989).

Hauck, "Engineer's Guide to Plastics," Materials Engineering 5(72):38-45 (Jul. 17, 1972).

Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).

(56) References Cited

OTHER PUBLICATIONS

Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill,F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Bouéet al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).
Chang et al., "Biodegradeable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das, S. et al., "Reviewing Antisense Oligonucleotide Therapy: Part 2, Delivery Issues," BioPharm, 2(11):44-51 (1999).
Dash, A. K. et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon, C. F. et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-smotic acutation of implantable insulin micropumps," J. Biomed. Materials Res. 17:931-943 (1983).
Efendic, S. et al., et al., "Overview of incretin hormones," Horm. Metab. Res., 36(11-12):742-746 (2004).
Eissele, R. et al., "Rat gastric somatostatin and gastrin release: interactions of exendin-4 and truncated glucagon-like peptide-1 (Glp-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng, J. et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng, J. et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon a-2b±ρ ribavirin therapy in patients with chronic hepatitis C," Prog. Abstr. 50th Annu. Mtg. Postgrad. Courses Am. Assn. Study Liver Dis., Dallas, Tx (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel TiazofurinAnalogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(12):121-128 (2002).
Luft et al., "Electro-osmotic valve for the controlled administration of drugs," Med. & Biological Engineering & Computing 45-50 (Jan. 1978) (non-English with English abstract).
Gan to Kagaku Ryoho, "Phase II study of recombinant leukocyte A interferon (Ro22-8181) in malignant brain tumors," Cancer & Chemotherapy 12(4):913-920 (Apr. 1985) (non-English with English abstract).

(56) References Cited

OTHER PUBLICATIONS

Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione, M., et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Goke, R. et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon $\alpha$-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-$\alpha$ plus N-acetyl cystein for chronic hepatitis C: a placebo controlled double-blind multicentre study," J. Med. Virol. 61(4):439-442 (Aug. 2000).
Gutniak, M. et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Heinrich, G. et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-$\alpha$ in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima, N. et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pp. (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferon$\beta$-1b is effective in relapsing-remitting multiple sclerosis," Neurology 43(4):655-667 (Apr. 1993).

INTERMUNE® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0/8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-$\gamma$," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic $\alpha$-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant $\alpha$-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon $\beta$-1b therapy in patients with MS," Neurology 54(1):193-199 (Jan. 2000).
Kronenberger et al., "Influence of interferon-$\alpha$ on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-$\omega$," J. Interferon Res. 14:57-59 (1994).
Kunzi et al., "Role of interferon-stimulated gene ISG-15 in the interferon-$\omega$-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatitis C: interferon alfa-2A trials," Hepatology 26: 89S-95S (Sep. 1997) (XP000981288).
Lopez, L. C. et al., "Mammalian pancreatic preproglucagon contains three glucagon-related peptides," Proc. Natl. Acad. Sci. USA, 80(18):5485-5489 (1983).
Lukaszewski et al., "Pegylated $\alpha$ interferon is an effective treatment for virulent Venezuelan equine encephalitis virus and has profound effects on host immune response to infection," J. Virol. 74(11):5006-5015 (Jun. 2000).

(56) References Cited

OTHER PUBLICATIONS

Lund, P. K. et al., "Pancreatic preproglucagon cDNA contains two glucagon-related coding sequences arranged in tandem," Proc. Natl. Acad. Sci. USA, 79(2):345-349 (1982).

Lundberg, "A submicron lipid emulsion coated with amphipathic polyethylene glycol for parenteral administration of paclitaxel (Taxol)," J. Pharm. & Pharmacol. 49(1):16-21 (1997).

Magnuson et al. "Enhanced recovery of a secreted mammalian protein from suspension culture of genetically modified tobacco cells," Protein Expression & Purification 7:220-228 (1996).

Malley et al., "Chronic Toxicity and Oncogenicity of N-Methylpyrrolidone (Nmp) In Rats and Mice by Dietary Administration," Drug Chem Toxicol. 24(4):315-38 (Nov. 2001).

Manning et al, "Stability of protein pharmaceuticals," Pharm. Res. 6(11):903-918 (1989).

Marincola et al., "Combination therapy with interferon alfa-2a and interleukin-2 for the treatment of metastatic cancer," J. Clinical Oncol. 13(5):1110-1122 (1995) (XP009078965).

Massey, "Interaction of vitamin E with saturated phospholipid bilayers," Biochem. & Biophys. Res. Comms. 106(3):842-847 (1982).

McHutchison et al., "Interferon α-2b alone or in combination with ribavirin as initial treatment for chronic hepatitis C," N. Engl. J. Med. 339(21):1485-1492 (Nov. 1998).

McHutchison, et al., "Open-label phase 1B study of hepatitis C viral dynamics with omega interferon treatment," Hepatology 34(4):A333 (Oct. 1, 2001) (XP004716177) (Abstract Only).

Meier, J. J. et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).

Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).

Milella et al., "Neutralizing antibodies to recombinant α-interferon and response to therapy in chronic hepatitis C infection," Liver 13(3):146-150 (Jun. 1993).

Mohler, "Primer on electrodeposited coatings," Materials Engineering 5:38-45 (1972).

Mojsov, S., "Structural requirements for biological activity of glucagon-like peptide-I," Int. J. Peptide Protein Research, 40:333-343 (1992).

Morgan, "Structure and Moisture Permeability of Film-Forming Poloyers," Ind. Eng. Chem. 45(10):2296-2306 (1953).

Motzer et al., "Phase I trial of 40-kd branched pegylated interferon alfa-2a for patients with advanced renal cell carcinoma," J. Clinical Oncol. 19(5):1312-1319 (2001).

Nauck, M. A. et al., "Normalization of fasting glycaemia by intravenous GLP-1 ([7-36 amide] or [7-37]) in type 2 diabetic patients," Diabet. Med., 15(11):937-945(1998).

Neumann et al., "Hepatitis C Viral Dynamics In Vivo and the Antiviral Efficacy of Interferon-alpha Therapy," Science 282:103-107 (Dec. 1998).

Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).

Norden et al., "Physicochemical characterization of a drug-containing phospholipid-stabilized o / w emulsion for intravenous administration," Eur. J. Pharm. Sci. 13(4):393-401 (2001).

Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).

Ortiz, A. et al., "A differential scanning calorimetry study of the interaction of α-tocopherol with mixtures of phospholipids," Biochim et Biophys Acta 898(2):214-222 (1987).

Panitch, "Interferons in multiple sclerosis," Drugs 44(6):946-962 (Dec. 1992).

Patzelt, C. et al., "Identification and processing of proglucagon in pancreatic islets," Nature, 282:260-266 (1979).

Peterson, R. G. et al., "Zucker Diabetic Fatty Rat as a Model for Non-insulin-dependent Diabetes Mellitus," ILAR Journal, 32(3):16-19 (1990).

Peterson, R. G. et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).

Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).

Plauth et al, "Open-label phase II study of omega interferon in previously untreated HCV infected patients," Hepatology 34(4):A331 (Oct. 1, 2001) (XP004716169) (Abstract Only).

Plauth et al, "Open-label study of omega interferon in previously untreated HCV-infected patients," J. Hepatology 36(Supp. 1):125 (Apr. 2002) (XP002511882) (Abstract Only).

Pohl, M. et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J. Biol. Chem., 273(16):9778-9784 (1998).

Poynard et al., "Is an 'a la carte' combined interferon α 2b plus ribavirin possible for the first line treatment in patients with chronic hepatitis C," Hepatology 31(1):211-218 (Jan. 2000).

Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).

"Intarcia Presents Positive ITCA 650 Phase 2 Study Results for Type 2 Diabetes at EASD,"Intarcia Therapeutics, Inc. (Sep. 22, 2010) (Press Release).

Quesada et al., "Interferons in Hematological Malignancies", eds. Baron et al., U. Tex. 487-495 (1987).

Quintanar-Guerrero et al., "Applications of the ion-pair concept to hydrophilic substances with special emphasis on peptides," Pharm. Res. 14(2):119-127 (1997).

Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).

Roche Pharmaceuticals, Roferon®-A (Interferon alfa-2a, recombinant), 22 pages (2003).

Roff et al., "Handbook of Common Polymers", Cleveland Rubber Co. 72 pages (1971).

Rogers et al., "Permeability Valves," Ind. & Eng. Chem. 49(11):1933-1936 (Nov. 17, 1957).

Roman et al., "Cholestasis in the rat by means of intravenous administration of cyclosporine vehicle, Cremophor EL," Transplantation 48(4);554-558 (1989).

Roth et al., "High Dose Etretinate and Interferon-alpha—A Phase I Study in Squamous Cell Carcinomas and Transitional Cell Carcinomas," Acta Oncol. 38(5):613-617 (1999).

Roth et al., "Combination therapy with amylin and peptide YY[3-36] in obese rodents: anorexigenic synergy and weight loss additivity," Endocrinol. 148(12):6054-61 (Dec. 2007).

Schepp, W. et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).

Schering Corp., Intron® A for Injection, 6 pages (2001).

Schering Corp., PEG-Intron™ (Peginterferon alfa-2b) Powder for Injection, 29 pages (2003).

(56) References Cited

OTHER PUBLICATIONS

Schmalfub, et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or ihterferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks, J. D. et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowskii et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski, M., et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania, T., et al., "Peripheral exendin-4 and peptide YY(3-36) synergistically reduce food intake through different mechanisms in mice," Endocrinology 146(9):3748-56 (Sep. 2005).
Tanaka, H., et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α2b therapy in chronic hepatitis C patients using viral and biochemical characteristics: a comparison," Hepatology 26(6):1640-01645 (Dec. 1997).
Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).
Tseng, C. C. et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, J. T., "Tympanic membrane perforations in the diabetic rat: a model of impaired wound healing," Otolaryngol. Head Neck Surg., 118(3 Pt. 1):304-308 (1998).
Wang et al., "Preferential interaction of a-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphatidylethanolamine," Biochimica et Biophysica Acta-Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (Macaca mulatta)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon α on viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).
Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).
Adolf, "Human interferon omega—a review." Mult. Sclr. 1:S44-47 (1995).
Costantino et al., "Protein Spray Freeze Drying. 2. Effect of Formulation Variables on particle Size and Stability," J. Pharm. Sci. 91:388-395 (2002).
Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).
Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).
Ishiwata et al., "Clinical effects of the recombinant feline interferon-omega on experimental parvovirus infection in beagle dogs," J. Vet. Med. Sci. 60(8):911-917 (1998).

(56) References Cited

OTHER PUBLICATIONS

Johnson et al., "How interferons fight disease," Sci. Am. 270(5):68-75 (May 1994).

Lublin et al., "Defining the clinical course of multiple sclerosis: results of an international survey," Neurology. 46:907-911 (1996).

Madsbad, "Exenatide and liraglutide: different approaches to develop GLP-1 receptor agonists (incretin rnimetics)—preclinical and clinical results," Best Practice & Research Clinical Endocrinology & Metabolism 23:463-77 (2009).

Nielsen, "Increfin rnimetics and DPP-IV inhibitors for the treatment of type 2 diabetes," Drug Discovery Today 10(10):703-710 (May 15, 2005).

Palmeri et al., "5-Fluorouracil and recombinant α-interferon-2a in the treatment of advanced colorectal carcinoma: a dose optimization study," J. Chemotherapy 2(5):327-330 (Oct. 1990).

Patti et al., "Natural interferon-b treatment of relapsing-remitting and secondary-progressive multiple sclerosis patients: two-year study," Acta. Neurol. Scand, 100:283-289 (1999).

Paty et al., "Interferon beta-1 b is effective in relapsing-remitting multiple sclerosis," Neurology 43:662-667 (1993).

PCT International Search Report for PCT/US2009/000916, 4 pages (Aug, 12, 2009).

"Intarcia Therapeutics Announces Final Results from a Phase 2 Study of Injectable Omega Interferon plus Ribavirin for the Treatment of Hepatits C Genotype-1 ," NLV Partners Press Coverage Portofolio News (Apr. 12, 2007) (Press Release).

Quianzon et al., "Lixisenatide-Once-daily Glucagon-like Peptide-1 Diabetes," US Endocrinology 7(2):104-109 (2011).

Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).

Roberts et al., "The Evolution of the Type I Interferons1," J. Interferon Cytokine Res. 18(10):805-816 (Oct. 1998).

Rohloff et al., "DUROS Technology Delivers Peptides and Proteins at Consistent Rate Continuously for 3 to 12 Months," J. Diabetes Sci. & Tech., 2(3):461-467 (May 1, 2008).

"Sequence Listings for International Patent Application Publication No. W02009109927, WIPO Patentscope", http://patentscope.wipo.int/search/docservicepdf_pctlid00000008776887, 1 page. (last visited Nov. 14, 2012).

Shire et al., "Challenges in the Development of High Protein Concentration Formulations," J. Pharm. Sci. 93:1390-1402 (2004).

Smith, "Peripheral Neuro-hormones as a Strategy to Treat Obesity," oral presentation at the 2007 Cardiometabolic Health Congress in Boston, MA, pp. 1-35 (Sep. 26-29, 2007).

Written Opinion for International Patent Application No. PCT/US2009/005629 (corresponding to U.S. Appl. No. 12/587,946), 5 pages (Apr. 15, 2011).

Zhang et al., "Efficacy observations of different dosages of interferon to treat 150 Hepatitis B carriers," Current Physician 2(12):45-46 (1997).

Pratley et al., "Targeting Incretins in Type 2 Diabetes: Role of GLP-1 Receptor Agonists and DPP-4 Inhibitors," Rev. Diabet. Stud., 5(2):73-94 (2008).

Sanofi-Aventis U.S. LLC, Prescribing Information for ADLYXIN® (Lixisenatide) Injection, for Subcutaneous Use, rev. Jul. 2016, 31 pages.

Amylin Pharmaceuticals, Inc., Prescribing Information for BYETTA® (Exenatide) Injection, rev. Oct. 2009, 34 pages.

AstraZeneca Pharmaceuticals LP, Prescribing Information for BYDUREONC® (Exenatide Extended-Release for Injectable Suspension), rev. Mar. 2015, 60 pages.

Novo Nordisk A/S, Prescribing Information for Victoza® (Liraglutide [rDNA Origin] Injection), Solution for Subcutaneous Use, v. 1, Jan. 2010, 23 pages.

GlaxoSmithKline LLC, Prescribing Information for TANZEUM® (Albiglutide) for Injection, for Subcutaneous Use, rev. Jun. 2014, 55 pages.

Eli Lilly & Company, Prescribing Information for TRULICITY® (Dulaglutide) Injection, for Subcutaneous Use, rev. Mar. 2015, 19 pages.

His-Ala-Glu-Gly-Thr-Phe-Thr-Ser-Asp-Val-
Ser-Ser-Tyr-Leu-Glu-Gly-Gln-Ala-Ala-Lys-
Glu-Phe-Ile-Ala-Trp-Leu-Val-Lys-Gly-Arg-NH$_2$

Figure 1A

His-Gly-Glu-Gly-Thr-Phe-Thr-Ser-Asp-Leu-
Ser-Lys-Gln-Met-Glu-Glu-Glu-Ala-Val-Arg-
Leu-Phe-Ile-Glu-Trp-Leu-Lys-Asn-Gly-Gly-
Pro-Ser-Ser-Gly-Ala-Pro-Pro-Pro-Ser-NH$_2$

Figure 1B

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

```
<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

OSMOTIC DELIVERY DEVICE COMPRISING AN INSULINOTROPIC PEPTIDE AND USES THEREOF

CROSS-REFERENCE TO RELATED APPLICATIONS

This application is a continuation of U.S. patent application Ser. No. 14/605,348, filed Jan. 26, 2015, which is a continuation of U.S. patent application Ser. No. 12/927,432, filed Nov. 15, 2010, now U.S. Pat. No. 8,940,316, which is a divisional of U.S. patent application Ser. No. 12/148,896, filed Apr. 22, 2008, now U.S. Pat. No. 8,299,025, which claims the benefit of U.S. Provisional Application Ser. No. 61/072,202, filed Mar. 28, 2008, and U.S. Provisional Application Ser. No. 60/926,005, filed Apr. 23, 2007, and which is a continuation-in-part of U.S. patent application Ser. No. 11/347,562, filed Feb. 3, 2006, now U.S. Pat. No. 8,114,437, which claims the benefit of U.S. Provisional Application No. 60/650,225, filed Feb. 3, 2005. Each of the above-referenced applications is herein incorporated by reference in its entirety.

SEQUENCE LISTING

The instant application contains a Sequence Listing which has been submitted in ASCII format via EFS-Web and is hereby incorporated by reference in its entirety. Said ACSII copy, created on Nov. 21, 2016, is named ITCA-036-C02US-SequenceListing-ST25.txt and is 1.41 kilobytes in size.

TECHNICAL FIELD

The present invention relates to organic chemistry, formulation chemistry, and peptide chemistry applied to pharmaceutical research and development. Aspects of the present invention provide suspension formulations of insulinotropic peptides for use in mammals and for the treatment of diseases or conditions.

BACKGROUND OF THE INVENTION

Glucagon-like peptide-1 (GLP-1) is 'important hormone and a fragment of the human proglucagon molecule. GLP-1 is rapidly metabolized by a peptidase (dipeptidylpeptidase IV or DPP-IV). A fragment of GLP-1, glucagon-like peptide-1 (7-36) amide (glucagon-like insulinotropic peptide, or GLIP) is a gastrointestinal peptide that potentiates the release of insulin in physiologic concentrations (Gutniak M., et al., N Engl J Med. 1992 May 14; 326(20):1316-22). GLP-1 and GLP-1(7-36)amide are incretins. Incretins are gastrointestinal hormones that cause an increase in the amount of insulin released from beta cells after eating.

Food intake, as well as stimulation of the sympathetic nervous system, stimulates secretion of GLP-1 in the small intestine of mammals. Further, GLP-1 stimulates the production and secretion of insulin, the release of somatostatin, glucose utilization by increasing insulin sensitivity, and, in animal studies, also stimulates beta-cell function and proliferation.

GLP-1(7-36)amide and GLP-1(7-37) normalize fasting hyperglycemia in Type 2 diabetic patients (Nauck, M. A., et al., Diabet. Med. 15(11):937-45(1998)).

Exendin-4 is an incretin mimetic (i.e., it mimics physiological effects of incretins) purified from *Heloderma suspectum* venom (Eng, J., et al., J. Biol. Chem. 267:7402-05 (1992)) and shows structural relationship to the incretin hormone GLP-1(7-36)amide. Exendin-4 and truncated exendin-(9-39)amide specifically interact with the GLP-1 receptor on insulinoma-derived cells and on lung membranes (Goke R, et al., J Biol. Chem. 268:19650-55 (1993)). Exendin-4 has approximately 53% homology to human GLP-1 (Pohl, M., et al., J Biol. Chem. 273:9778-84 (1998)). Unlike GLP-1, however, exendin-4 is resistant to degradation by DPP-IV. A glycine substitution confers resistance to degradation by DPP-IV (Young, A. A., et al., Diabetes 48(5):1026-34(1999)).

SUMMARY OF THE INVENTION

The present invention relates to suspension formulations comprising a particle formulation and a suspension vehicle, as well as devices comprising such formulations, methods of making such formulations and devices, and methods of use thereof.

In one aspect, the present invention relates to a suspension formulation comprising, a particle formulation comprising an insulinotropic peptide and one or more stabilizer selected from the group consisting of carbohydrates, antioxidants, amino acids, buffers, and inorganic compounds. The suspension formulation further comprises a non-aqueous, single-phase suspension vehicle comprising one or more polymer and one or more solvent. The suspension vehicle exhibits viscous fluid characteristics and the particle formulation is dispersed in the vehicle.

In one embodiment, the suspension formulation comprises a particle formulation comprising an insulinotropic peptide, a disaccharide (e.g., sucrose), methionine, and a buffer (e.g., citrate), and a non-aqueous, single-phase suspension vehicle comprising one or more pyrrolidone polymer (e.g., polyvinylpyrollidone) and one or more solvent (e.g., lauryl lactate, lauryl alcohol, benzyl benzoate, or mixtures thereof.

Examples of insulinotropic peptides include, but are not limited to, glucagon-like peptide-1 (GLP-1), exenatide, and derivatives or analogues thereof. In one embodiment of the invention, the insulinotropic peptide is GLP-1(7-36)amide. In another embodiment of the invention, the insulinotropic peptide is exenatide.

The particle formulations of the present invention may further comprise a buffer, for example, selected from the group consisting of citrate, histidine, succinate, and mixtures thereof.

The particle formulations of the present invention may further comprise an inorganic compound, for example, selected from the group consisting of citrate, histidine, succinate, and mixtures thereof NaCl, $Na_2SO_4$, $NaHCO_3$, KCl, $KH_2PO_4$, $CaCl_2$, and $MgCl_2$.

The one or more stabilizer in the particle formulations may comprise, for example, a carbohydrate selected from the group consisting of lactose, sucrose, trehalose, mannitol, cellobiose, and mixtures thereof.

The one or more stabilizer in the particle formulations may comprise, for example, an antioxidant selected from the group consisting of methionine, ascorbic acid, sodium thiosulfate, ethylenediaminetetraacetic acid (EDTA), citric acid, cysteins, thioglycerol, thioglycolic acid, thiosorbitol, butylated hydroxanisol, butylated hydroxyl toluene, and propyl gallate, and mixtures thereof.

The one or more stabilizer in the particle formulations may comprise an amino acid.

In one embodiment, the solvent of the suspension vehicle of the present invention is selected from the group consisting of lauryl lactate, lauryl alcohol, benzyl benzoate, and mixtures thereof. An example of a polymer that can be to formulate the suspension vehicle is a pyrrolidone (e.g., polyvinylpyrrolidone). In a preferred embodiment, the polymer is a pyrrolidone and the solvent is benzyl benzoate.

The suspension formulation typically has an overall moisture content less than about 10 wt % and in a preferred embodiment less than about 5 wt %.

An implantable drug delivery device may be used to contain and deliver the suspension formulation of the present invention. In one embodiment the device is an osmotic delivery device.

The suspension formulations of the present invention can be used to treat any of a number of disease states or conditions in a subject in need of treatment, for example, type II diabetes. In one embodiment, an implantable drug delivery device delivers a suspension formulation of the present invention at a substantially uniform rate for a period of about one month to about a year. The device may, for example, be implanted subcutaneously in a convenient location.

The present invention also includes methods of manufacturing the suspension formulations, particle formulations, suspension vehicles, and devices of the present invention as described herein.

These and other embodiments of the present invention will readily occur to those of ordinary skill in the art in view of the disclosure herein.

BRIEF DESCRIPTION OF THE FIGURES

FIGS. 1A and 1B presents the sequences of two examples of insulinotropic peptides: FIG. 1A, glucagon-like peptide 1 (7-36) amide (GLP-1(7-36)amide) (SEQ ID NO:1), and FIG. 1B, synthetic exenatide peptide (SEQ ID NO:2).

DETAILED DESCRIPTION OF THE INVENTION

Figure 2:
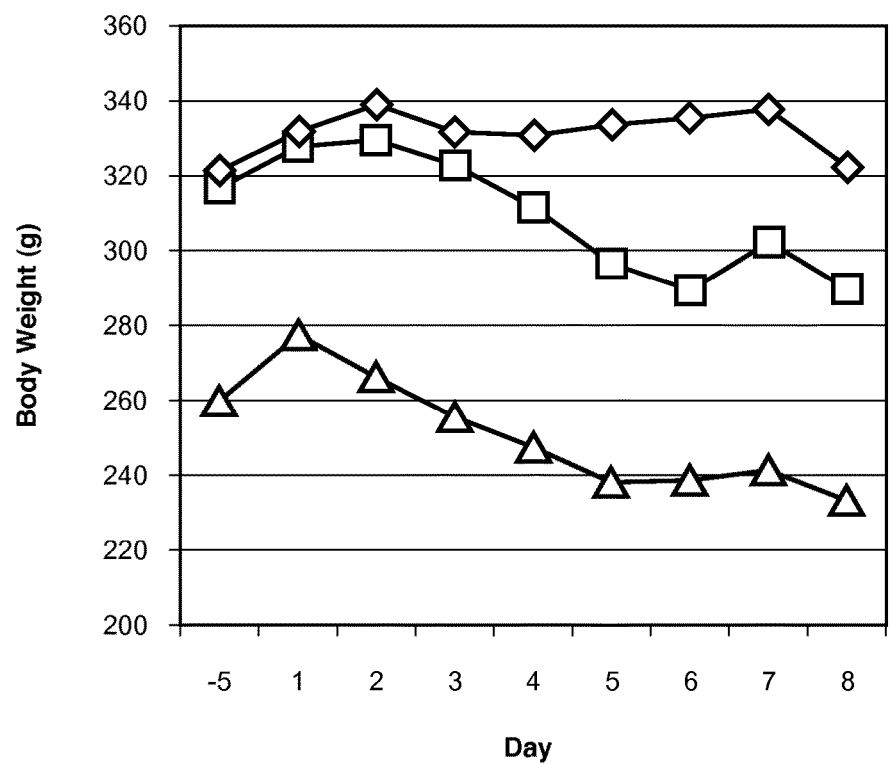
FIG. 2 presents data for group mean body weights of test animals treated by continuous delivery of exenatide from a DUROS® (ALZA Corporation, Mountain View, Calif., licensed to Intarcia Therapeutics, Inc., Hayward, Calif.) device. In the figure, the vertical axis is mean body weight in grams (Body Weight (g)) and the horizontal axis is the day (Day). The obese animals of Group 1 (closed diamonds) were the control group to which 0 mcg of exenatide from a DUROS® device was administered per day. The animals of Group 2 (closed squares) were obese animals to which 20 mcg of exenatide from a DUROS® device was administered per day. The animals of Group 3 (closed triangles) were lean animals to which 20 mcg of exenatide was administered per day.

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, mixtures of peptides, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "peptide," "polypeptide," and "protein" are used interchangeable herein and typically refer to a molecule comprising a chain of two or more amino acids (e.g., most typically L-amino acids, but also including, e.g., D-amino acids, modified amino acids, amino acid analogues, and/or amino acid mimetic). Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl).

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotropic" as used herein refers to the ability of a compound, e.g., a peptide, to stimulate or affect the production and/or activity of insulin (e.g., an insulinotropic hormone). Such compounds typically stimulate the secretion or biosynthesis of insulin in a subject.

The phrase "insulinotropic peptide" as used herein includes, but is not limited to, glucagon-like peptide 1 (GLP-1), as well as derivatives and analogues thereof, and exenatide, as well as derivatives and analogues thereof.

The term "vehicle" as used herein refers to a medium used to carry a compound. Vehicles of the present invention typically comprise components such as polymers and solvents. The suspension vehicles of the present invention typically comprise solvents and polymers that are used to prepare suspension formulations of polypeptide particles.

The phrase "phase separation" as used herein refers to the formation of multiple phases (e.g., liquid or gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a peptide, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where $F/A$=shear stress (force per unit area),
$\mu$=a proportionality constant (viscosity), and
$V/L$=the velocity per layer thickness (shear rate).

From this relationship, the ratio of shear stress to shear rate defines viscosity. Measurements of shear stress and shear rate are typically determined using parallel plate rheometery performed under selected conditions (for example, a temperature of about 37° C.). Other methods for the determination of viscosity include, measurement of a kinematic viscosity using a viscometers, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, preferably less than or equal to about 5 wt %, and more preferably less than about 4 wt %.

The term "subject" as used herein refers to any member of the subphylum chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The terms "drug," "therapeutic agent", and "beneficial agent" are used interchangeably to refer to any therapeutically active substance that is delivered to a subject to produce a desired beneficial effect. In one embodiment of the present invention, the drug is an insulinotropic peptide, e.g., GLP-1, exenatide, and derivatives or analogues thereof. The devices and methods of the present invention are well suited for the delivery of polypeptides as well as small molecules and combinations thereof.

The term "osmotic delivery device" as used herein typically refers to a device used for delivery of one or more beneficial agent (e.g., an insulinotropic peptide) to a subject, wherein the device comprises, for example, a reservoir (made, for example, from a titanium alloy) having a lumen that contains a suspension formulation (e.g., comprising an insulinotropic peptide) and an osmotic agent formulation. A piston assembly positioned in the lumen isolates the suspension formulation from the osmotic agent formulation. A semi-permeable membrane positioned at a first distal end of the reservoir adjacent the osmotic agent formulation, as well as a flow modulator (which defines a delivery orifice through which the suspension formulation exits the device) that is positioned at a second distal end of the reservoir adjacent the suspension formulation. Typically, the osmotic delivery device is implanted within the subject, for example, subcutaneously (e.g., in the inside, outside, or back of the upper arm; or in the abdominal area).

2.0.0 General Overview of the Invention

Before describing the present invention in detail, it is to be understood that this invention is not limited to particular types of drug delivery, particular types of drug delivery devices, particular sources of peptides, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In one aspect, the present invention relates to a suspension formulation, comprising a particle formulation and a suspension vehicle. The particle formulation includes, but is not limited to, an insulinotropic peptide and one or more stabilizer. The one or more stabilizer is typically selected from the group consisting of carbohydrates, antioxidants, amino acids, and buffers. The suspension vehicle is typically a non-aqueous, single-phase suspension vehicle comprising one or more polymer and one or more solvent. The suspension vehicle exhibits viscous fluid characteristics. The particle formulation is uniformly dispersed in the vehicle.

In one embodiment of the present invention the insulinotropic peptide is a glucagon-like peptide-1 (GLP-1), a derivative of GLP-1 (e.g., GLP-1(7-36)amide), or an analogue of GLP-1.

In another embodiment of the present invention insulinotropic peptide is exenatide, a derivative of exenatide, or an analogue of exenatide.

The particle formulation of the present invention typically includes one or more of the following stabilizers: one or more carbohydrate (e.g., a disaccharide, such as, lactose, sucrose, trehalose, cellobiose, and mixtures thereof); one or more antioxidant (e.g., methionine, ascorbic acid, sodium thiosulfate, ethylenediaminetetraacetic acid (EDTA), citric acid, butylated hydroxyltoluene, and mixtures thereof); and one or more buffer (e.g., citrate, histidine, succinate, and mixtures thereof). In a preferred embodiment, the particle formulation comprises an insulinotropic peptide, sucrose, methionine, and citrate buffer. The ratio of insulinotropic peptide to sucrose+methionine is typically about 1/20, about 1/10, about 1/5, about 1/2, about 5/1, about 10/1, or about 20/1, preferably between about 1/5 to 5/1, more preferably between about 1/3 to 3/1. The particle formulation is preferably a particle formulation prepared by spray drying and has a low moisture content, preferably less than or equal to about 10 wt %, more preferably less or equal to about 5 wt %. In another embodiment the particle formulation can be lyophilized.

The suspension vehicle of the present invention comprises one or more solvent and one or more polymer. Preferably the solvent is selected from the group consisting of lauryl lactate, lauryl alcohol, benzyl benzoate, and mixtures thereof. More preferably the solvent is lauryl lactate or benzyl benzoate. Preferably the polymer is a pyrrolidone. In some embodiments the polymer is polyvinylpyrrolidone (e.g., polyvinylpyrrolidone K-17, which typically has an approximate average molecular weight range of 7,900-10,800). In one embodiment of the present invention the solvent consists essentially of benzyl benzoate and polyvinylpyrrolidone.

The suspension formulation typically has a low overall moisture content, for example, less than or equal to about 10 wt % and in a preferred embodiment less than or equal to about 5 wt %.

In another aspect, the present invention relates to an implantable drug delivery device, comprising a suspension formulation of the present invention. In a preferred embodiment, the drug delivery device is an osmotic delivery device.

The present invention further includes methods of manufacturing the suspension formulations of the present invention, as well as osmotic delivery devices loaded with a suspension formulation of the present invention. In one embodiment, the present invention includes a method of manufacturing an osmotic delivery device comprising, loading a suspension formulation into a reservoir of the osmotic delivery device.

In another aspect, the present invention relates to a method of treating diabetes (e.g., diabetes mellitus type 2 or gestational diabetes) in a subject in need of such treatment, comprising delivering a suspension formulation of the present invention from an osmotic delivery device at a substantially uniform rate. Typically the suspension formulation is delivered for a period of about one month to about a year, preferably about three months to about a year. The method may further include subcutaneously inserting an osmotic delivery device, loaded with a suspension formulation of the present invention, into the subject.

In further aspects, the present invention relates to methods of stimulating insulin secretion, suppressing glucagon secretion, slowing gastric emptying, treating diabetic related disorders, treating hyperglycemia, treating obesity, controlling appetite, reducing weight, and regulating gastrointestinal motility.

2.1.0 Formulations and Compositions 2.1.1 Particle Formulations

In one aspect, the present invention provides a pharmaceutical composition comprising a suspension formulation of an insulinotropic peptide, for example, GLP-1 or exenatide. The suspension formulation comprises a non-aqueous, single-phase vehicle including at least one polymer and at least one solvent. The vehicle preferably exhibits viscous fluid characteristics. The peptide component comprises the insulinotropic peptide in a particle formulation that is dispersed in the vehicle. Typically, the particle formulation includes a stabilizing component comprising one of more stabilizer component selected from the group consisting of carbohydrates, antioxidants, amino acids, buffers, and inorganic compounds.

Insulinotropic peptides useful in the practice of the present invention include, but are not limited to, GLP-1 and exenatide.

Bell, G. I., et al., (Nature 302:716-718 (1983)) discovered that proglucagon (Lund, et al., Proc. Natl. Acad. Sci. U.S.A. 79:345-349 (1982); Patzelt, et al., Nature, 282:260-266 (1979)) contained three discrete, highly homologous peptide regions which were designated glucagon, glucagon-like peptide 1 (GLP-1), and glucagon-like peptide 2 (GLP-2). Lopez, et al., (Proc. Natl. Acad. Sci. U.S.A. 80:5485-5489 (1983)) demonstrated that the peptide sequence of GLP-1 was a sequence of 37 amino acids and that the peptide sequence of GLP-2 was a sequence of 34 amino acids.

Studies of the structure of rat preproglucagon revealed a similar pattern of proteolytic cleavage resulting in the formation of glucagon, GLP-1, and GLP-2 (Heinrich, G., et al., Endocrinol., 115:2176-2181 (1984)). Human, rat, bovine, and hamster sequences of GLP-1 were found to be identical (Ghiglione, M., et al., Diabetologia, 27:599-600 (1984)).

Cleavage of preproglucagon first yields GLP-1(1-37), a 37 amino acid peptide that has poor insulinotropic activity. A subsequent cleavage of the peptide bond between amino acid residues 6 and 7 produces a biologically active GLP-1 referred to as GLP-1(7-37) (by convention the amino terminus of GLP-1(7-37) was assigned number 7 and the carboxy terminus number 37). Approximately 80% of GLP-1(7-37) that is produced in mammals is amidated at the C-terminus after removal of the terminal glycine residue in L-cells, resulting in GLP-1(7-36)amide. The biological effects and metabolic turnover of the free acid GLP-1(7-37), and the amide, GLP-1(7-36)amide, are essentially the same. The sequence of GLP-1(7-36)amide is presented in FIG. 1A.

GLP-1 (including three forms of the peptide, GLP-1(1-37), GLP-1(7-37) and GLP-1(7-36)amide, as well as analogs of GLP-1) have been shown to stimulate insulin secretion (i.e., it is insulinotropic) which induces glucose uptake by cells and results in decreases in serum glucose levels (see, e g., Mojsov, S., Int. J. Peptide Protein Research, 40:333-343 (1992)). Another GLP-1 analogue is liraglutide, which is a long-acting DPP-4-resistant GLP-1 receptor agonist. Liraglutide has 97% identity to GLP-1(7-37). Liraglutide is also called NN-2211 and [Arg34, Lys26]-(N-epsilon-(gamma-Glu(N-alpha-hexadecanoyl))-GLP-1(7-37) (see, e.g., U.S. Pat. No. 6,969,702).

Numerous GLP-1 derivatives and analogues demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217). Accordingly, for ease of discussion herein, the family of GLP-1 derivatives and analogues having insulinotropic activity is referred to collectively as GLP-1.

Gastric inhibitory peptide (GIP) is also an insulinotropic peptide (Efendic, S., et al., Horm Metab Res. 36:742-6 (2004)). GIP is a hormone secreted by the mucosa of the duodenum and jejunum in response to absorbed fat and carbohydrate that stimulate the pancreas to secrete insulin. GIP is also known as glucose-dependent insulinotropic polypeptide. GIP is a 42-amino acid gastrointestinal regulatory peptide that stimulates insulin secretion from pancreatic beta cells in the presence of glucose (Tseng, C., et al., PNAS 90:1992-1996 (1993)).

The exendins are peptides that were isolated from the venom of the Gila-monster. Exendin-4 is present in the venom of *Heloderma suspectum* (Eng, J., et al., J. Biol. Chem., 265:20259-62 (1990); Eng., J., et al., J. Biol. Chem., 267:7402-05 (1992); U.S. Pat. No. 5,424,286). The exendins have some sequence similarity to several members of the glucagon-like peptide family, with the highest homology, 53%, being to GLP-1(7-36)amide (Goke, et al., J. Biol. Chem., 268:19650-55 (1993)).

Exendin-4 acts at GLP-1 receptors on insulin-secreting beta-TC1 cells, dispersed acinar cells from guinea pig pancreas, and parietal cells from stomach. The exendin-4 peptide also stimulates somatostatin release and inhibits gastrin release in isolated stomachs (Goke, et al., J. Biol. Chem. 268:19650-55 (1993); Schepp, et al., Eur. J. Pharmacol., 69:183-91 (1994); Eissele, et al., Life Sci., 55:629-34 (1994)). Based on their insulinotropic activities, use of exendin-3 and exendin-4 for the treatment of diabetes mellitus and the prevention of hyperglycemia has been proposed (U.S. Pat. No. 5,424,286).

Numerous exendin-4 derivatives and analogues (including, e.g., exendin-4 agonists) demonstrating insulinotropic action are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). Exenatide is a synthetic peptide having the same 39 amino acid sequence as exendin-4. Exenatide is a peptide incretin mimetic that exhibits glucoregulatory activities similar to the mammalian incretin hormone glucagon-like peptide 1 (GLP-1). Incretin hormones are hormones that cause an increase in the amount of insulin released when glucose levels are normal or particularly when they are elevated. Incretin hormones affect other activities defined by insulin secretion, for example, they can reduce glucagon production and delay gastric emptying. Further, incretin hormones may improve insulin sensitivity and possibly increase islet cell neogenesis.

For ease of discussion herein, the family of exendin-4 peptides, including synthetic versions (e.g., exenatide), derivatives and analogues having insulinotropic activity, is referred to collectively as exenatide.

In one aspect, the present invention provides particle formulations of insulinotropic peptides that can be used to prepare suspension formulations. The insulinotropic peptides of the present invention shall not be limited by method of synthesis or manufacture and shall include those obtained from natural sources, or synthesized or manufactured by recombinant (whether produced from cDNA or genomic DNA), synthetic, transgenic, and gene-activated methods. In preferred embodiments of the present invention the insulinotropic peptide is a GLP-1 peptide or an exendin peptide (as described herein above), for example, GLP-1(7-36) amide or exenatide. The present invention also includes combinations of two or more insulinotropic peptides, for example, GLP-1(7-36)amide and GIP.

Particle formulations of the invention are preferably chemically and physically stable for at least 1 month, preferably at least 3 months, more preferably at least 6 months, more preferably at least 12 months at delivery temperature. The delivery temperature is typically normal human body temperature, for example, about 37° C., or slightly higher, for example, about 40° C. Further, particle formulations of the present invention are preferably chemically and physically stable for at least 3 months, preferably at least 6 months, more preferably at least 12 months, at storage temperature. Examples of storage temperatures include refrigeration temperature, for example, about 5° C., or room temperature, for example, about 25° C.

A particle formulation may be considered chemically stable if less than about 25%, preferably less than about 20%, more preferably less than about 15%, more preferably less than about 10%, and more preferably less than about 5% breakdown products of the peptide particles are formed after about 3 months, preferably after about 6 months, preferably after about 12 months at delivery temperature and after about 6 months, after about 12 months, and preferably after about 24 months at storage temperature.

A particle formulation may be considered physically stable if less than about 10%, preferably less than about 5%, more preferably less than about 3%, more preferably less than 1% aggregates of the peptide particles are formed after about 3 months, preferably after about 6 months, at delivery temperature and about 6 months, preferably about 12 months, at storage temperature.

To preserve protein stability generally an insulinotropic peptide solution is kept in a frozen condition and lyophilized or spray dried to a solid state. Tg (glass transition temperature) may be one factor to consider in achieving stable compositions of peptide. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. No mobility of molecules correlates with no instability issues. Tg is also dependent on the moisture level in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. The particles are preferably substantially uniform in shape and size.

A typical spray dry process may include, for example, loading a spray solution containing a peptide, for example, an insulinotropic peptide (e.g., GLP-1(7-36)amide or exenatide), and stabilizing excipients into a sample chamber. The sample chamber is typically maintained at a desired temperature, for example, refrigeration to room temperature. Refrigeration generally promotes stability of the protein. A solution, emulsion, or suspension is introduced to the spray dryer where the fluid is atomized into droplets. Droplets can be formed by use of a rotary atomizer, pressure nozzle, pneumatic nozzle, or sonic nozzle. The mist of droplets is immediately brought into contact with a drying gas in a drying chamber. The drying gas removes solvent from the droplets and carries the particles into a collection chamber. In spray drying, factors that can affect yield include, but are not limited to, localized charges on particles (which may promote adhesion of the particles to the spray dryer) and aerodynamics of the particles (which may make it difficult to collect the particles). In general, yield of the spray dry process depends in part on the particle formulation.

In one embodiment of the present invention, the particles are sized such that they can be delivered via an implantable drug delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, preferably is less than about 20%, more preferably is less than about than 10%, of the diameter of the delivery orifice. In an embodiment of the particle formulation for use with an osmotic delivery system, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns. In one embodiment, the orifice is about 0.25 mm (250 µm) and the particle size is approximately 3-5 µm.

In a preferred embodiment, when the particles are incorporated in a suspension vehicle they do not settle in less than about 3 months at delivery temperature. Generally speaking, smaller particles tend to have a lower settling rate in viscous suspension vehicles than larger particles. Accordingly, micron- to nano-sized particles are typically desirable. In an embodiment of the particle formulation of the present invention for use in an implantable osmotic delivery device, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns.

In one embodiment, a particle formulation of the present invention comprises one or more insulinotropic peptide, as described above, one or more stabilizers, and optionally a buffer. The stabilizers may be, for example, carbohydrate, antioxidant, amino acid, buffer, or inorganic compound. The amounts of stabilizers and buffer in the particle formulation can be determined experimentally based on the activities of the stabilizers and buffers and the desired characteristics of the formulation. Typically, the amount of carbohydrate in the formulation is determined by aggregation concerns. In general, the carbohydrate level should not be too high so as to avoid promoting crystal growth in the presence of water due to excess carbohydrate unbound to insulinotropic peptide. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize insulinotropic peptide during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, trytophan, serine, asparagines, cysteine, tyrosine, lysine, and norleucine. Preferred amino acids include those that readily oxidize, e.g., cysteine, methionine, and trytophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, $Na_2SO4$, $NaHCO_3$, KCl, $KH_2PO4$, $CaCl_2$, and $MgCl_2$.

In addition, the particle formulation may include other excipients, such as surfactants, bulking agents, and salts. Examples of surfactants include, but are not limited to, Polysorbate 20, Polysorbate 80, PLURONIC® (BASF Corporation, Mount Olive, N.J.) F68, and sodium docecyl sulfate (SDS). Examples of bulking agents include, but are not limited to, mannitol and glycine. Examples of salts include, but are not limited to, sodium chloride, calcium chloride, and magnesium chloride.

All components included in the particle formulation are typically acceptable for pharmaceutical use in mammals, in particular, in humans.

Table 1 below presents examples of particle formulation composition ranges for particles comprising exenatide.

TABLE 1

|  | Range (% by weight) | Preferred Range (% by weight) | More Preferred Range (% by weight) |
| --- | --- | --- | --- |
| Particle loading in suspension formulation In Particles | 0.1 to 99.9% | 1 to 50% | 5 to 40% |
| Exenatide peptide | 1 to 99% | 5 to 70% | 10 to 60% |
| Carbohydrate | 0 to 99% | 2.5 to 40% | 5 to 30% |
| Antioxidant and/ or amino acid | 0 to 99% | 2.5 to 30% | 5 to 30% |
| Buffer | 0 to 99% | 10 to 80% | 10 to 70% |

In one embodiment, the exenatide particle formulation comprises exenatide peptide, sucrose (carbohydrate), methionine (antioxidant), and sodium citrate/citric acid (citrate buffer).

Table 2 below presents examples of particle formulation composition ranges for particles comprising GLP-1.

TABLE 2

|  | Range (% by weight) | Preferred Range (% by weight) | More Preferred Range (% by weight) |
| --- | --- | --- | --- |
| Particle loading in suspension formulation In Particles | 0.1 to 99.9% | 1 to 50% | 10-50% |
| GLP-1 peptide | 1 to 99% | 5 to 95% | 30-90% |
| Carbohydrate and/or Antioxidant and/ or amino acid | 0 to 99% | 0.1 to 30% | 2-20% |
| Buffer | 0 to 99% | 0.1 to 50% | 2-30% |

Within these weight percent ranges for components of the particle formulation, some preferred component ratios are as follows: insulinotropic peptide (e.g., exenatide or GLP-1) to antioxidant (e.g., methionine)—1/10, 1/5, 1/2.5, 1/1, 2.5/1, 5/1, 10/1, preferably between about 1/5 to 5/1, more preferably between about 1/3 to 3/1 (these same component ratios apply to insulinotropic peptide to amino acid ratios); insulinotropic peptide (e.g., exenatide or GLP-1) to carbohydrate (e.g., sucrose)—1/10, 1/5, 1/2.5, 1/1, 2.5/1, 5/1, 10/1, preferably between about 1/5 to 5/1, more preferably between about 1/3 to 3/1; and/or insulinotropic peptide (e.g., exenatide or GLP-1) to antioxidant+carbohydrate (e.g., methionine+sucrose)—1/20, 1/10, 1/5, 1/2, 5/1, 10/1, 20/1, preferably between about 1/5 to 5/1, more preferably between about 1/3 to 3/1 (these same component ratios apply to insulinotropic peptide to amino acid+carbohydrate ratios). The present invention also includes ranges corresponding to all of these ratios, for example, between about 1/20 and about 20/1, between about 1/10 and about 10/1, between about 1/5 and about 5/1, and so on, as well as, for example, between about 1/5 and about 3/1, and so on.

In summary, insulinotropic peptides are formulated into dried powders in solid state, which preserve maximum chemical and biological stability of proteins or peptides. The particle formulation offers long term storage stability at high temperature, and therefore, allows delivery to a subject of stable and biologically effective peptide for extended periods of time.

Particle size distribution of the dry particle powder can be well controlled (0.1 micron—20 micron), for example, by using the methods of spray drying or lyophilization to prepare the particle formulations. The process parameters for formation of the dry powder are optimal to produce particles with desired particle size distribution, density, and surface area.

The selected excipients and buffer in the particle formulation may provide, for example, the following functions: density modification of the dry powder; preservation of the peptide chemical stability; maintenance of the peptide's physical stability (e.g., high glass transition temperature, and avoiding phase to phase transition); producing homogenous dispersions in suspension by use of bulking agents; modification of hydrophobicity and/or hydrophilicity to manipulate dry powder solubility in selected solvents; and, manipulation of pH during processing and maintenance of pH in the product (for solubility and stability).

The particle formulations of the present invention are exemplified herein below with reference to exenatide and GLP-1(7-36)amide as exemplary insulinotropic peptides (see, Example 1 and Example 2). These examples are not intended to be limiting.

2.1.2 Vehicle and Suspension Formulations

In one aspect of the present invention, the suspension vehicle provides a stable environment in which the insulinotropic peptide particle formulation is dispersed. The particle formulations are chemically and physically stable (as described above) in the suspension vehicle. The suspension vehicle typically comprises one or more polymers and one or more solvents that form a solution of sufficient viscosity to uniformly suspend the particles comprising the insulinotropic peptide.

The viscosity of the suspension vehicle is typically sufficient to prevent the particle formulation from settling during storage and use in a method of delivery, for example, in an implantable, drug delivery device. The suspension vehicle is biodegradable in that the suspension vehicle disintegrates or breaks down over a period of time in response to a biological environment. The disintegration of the suspension vehicle may occur by one or more physical or chemical degradative processes, such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the patient.

The solvent in which the polymer is dissolved may affect characteristics of the suspension formulation, such as the behavior of the insulinotropic peptide particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. However, typically the insulinotropic peptide is substantially insoluble in the solvent. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and combinations thereof.

Examples of polymers for formulation of the suspension vehicles of the present invention include, but are not limited to, a polyester (e.g., polylactic acid or polylacticpolyglycolic acid), pyrrolidone (e.g., polyvinylpyrrolidone (PVP) having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. In one embodiment, the polymer is PVP having a molecular weight of 2,000 to 1,000,000. In a preferred embodiment the polymer is polyvinylpyrrolidone K-17 (typically having an approximate average molecular weight range of 7,900-10,800). Polyvinylpyrrolidone can be characterized by its K-value (e.g., K-17), which is a viscosity index. The polymer used in the suspension vehicle may include one or more different polymers or may include different grades of a single polymer. The polymer used in the suspension vehicle may also be dry or have a low moisture content.

Generally speaking, a suspension vehicle according to the present invention may vary in composition based on the desired performance characteristics. In one embodiment, the suspension vehicle may comprise about 40% to about 80% (w/w) polymer(s) and about 20% to about 60% (w/w) solvent(s). Preferred embodiments of a suspension vehicle include vehicles formed of polymer(s) and solvent(s) combined at the following ratios: about 25% solvent and about 75% polymer; about 50% solvent and about 50% polymer; about 75% solvent and about 25% polymer.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the insulinotropic peptide at a desired rate. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. The viscosity may be measured at 37° C., at a shear rate of $10^{-4}$/sec, using a parallel plate rheometer. In some embodiments, the viscosity of the suspension vehicle ranges from approximately 5,000 poise to approximately 50,000 poise. In preferred embodiments, the viscosity range is between about 12,000 to about 18,000 poise at 33° C.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The particle formulation, comprising an insulinotropic peptide, is added to the suspension vehicle to form a suspension formulation. The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

The suspension formulations of the present invention are exemplified herein below with reference to exenatide and GLP-1(7-36)amide as exemplary insulinotropic peptides (see, Example 3 and Example 4). These examples are not intended to be limiting.

In summary, the components of the suspension vehicle provide biocompatibility. Components of the suspension vehicle offer suitable chemico-physical properties to form stable suspensions of, for example, dry powder particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

3.0.0 Delivery of Suspension Formulations

The suspension formulations described herein may be used in an implantable, drug delivery device to provide sustained delivery of a compound over an extended period of time, such as over weeks, months, or up to about one year. Such an implantable drug delivery device is typically capable of delivering the compound at a desired flow rate over a desired period of time. The suspension formulation may be loaded into the implantable, drug delivery device by conventional techniques.

The suspension formulation may be delivered, for example, using an osmotically, mechanically, electromechanically, or chemically driven drug delivery device. The insulinotropic peptide is delivered at a flow rate that is therapeutically effective to the subject in need of treatment by the insulinotropic peptide.

The insulinotropic peptide may be delivered over a period ranging from more than about one week to about one year or more, preferably for about one month to about a year or more, more preferably for about three months to about a year or more. The implantable, drug delivery device may include a reservoir having at least one orifice through which the insulinotropic peptide is delivered. The suspension formulation may be stored within the reservoir. In one embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005-0175701, 2007-0281024, and 2008-0091176).

The DUROS® delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a therapeutic agent at a predetermined rate based on the principle of osmosis. Extracellular fluid enters the DUROS® device through a semipermeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation of the present invention, comprising, for example, GLP-1 (7-36)amide or exenatide, wherein the device is capable of delivering the suspension formulation to a subject over an extended period of time (e.g., about 3, about 6, or about 12 months) at a predetermined, therapeutically effective delivery rate.

Implantable devices, for example, the DUROS® device, provide the following advantages for administration of a beneficial agent formulation: true zero-order release of the beneficial agent pharmacokinetically; long-term release period time (e.g., up to about 12 months); and reliable delivery and dosing of a beneficial agent.

Other implantable, drug delivery devices may be used in the practice of the present invention and may include regulator-type implantable pumps that provide constant flow, adjustable flow, or programmable flow of the compound, such as those available from Codman & Shurtleff, Inc. (Raynham, Mass.), Medtronic, Inc. (Minneapolis, Minn.), and Tricumed Medinzintechnik GmbH (Germany).

Implantable devices, for example, the DUROS® device, provide the following advantages for administration of the suspension formulations of the present invention: true zero-order release of the insulinotropic peptide pharmacokinetically; long-term release period time (e.g., up to about 12 months); and reliable delivery and dosing of the insulinotropic peptide.

The amount of beneficial agent employed in the delivery device of the invention is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Typically, for an osmotic delivery device, the volume of a beneficial agent chamber comprising the beneficial agent formulation is between about 100 μl to about 1000 μl, more preferably between about 120 μl and about 500 μl, more preferably between about 150 μl and about 200 μl.

Typically, the osmotic delivery device is implanted within the subject, for example, subcutaneously. The device(s) can be inserted in either or both arms (e.g., in the inside, outside, or back of the upper arm) or into the abdomen. Preferred locations in the abdomen are under the abdominal skin in the area extending below the ribs and above the belt line. To provide a number of locations for insertion of one or more osmotic delivery device within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions.

The suspension formulation may also be delivered from a drug delivery device that is not implantable or implanted, for example, an external pump such as a peristaltic pump used for subcutaneous delivery in a hospital setting.

The suspension formulations of the present invention may also be used in infusion pumps, for example, the ALZET® (DURECT Corporation, Cupertino Calif.) osmotic pumps which are miniature, infusion pumps for the continuous dosing of laboratory animals (e.g., mice and rats).

The suspension formulations of the present invention may also be used in the form of injections to provide highly concentrated bolus doses of biologically active insulinotropic peptides.

In one embodiment of the present invention, the continuous delivery of, for example, derivatives and analogues of GLP-1 that have short half-lives after injection into humans (e.g., GLP-1(7-36)amide or exenatide) from an implantable device would be particularly beneficial. Further, the use of an implantable device, such as the DUROS® device, to deliver insulinotropic peptides could reduce injection-related side-effects and, with increased convenience of dosing, result in increased treatment compliance. The duration of drug delivery from one implant may be weeks or as long as one year.

Some advantages and benefits of the suspension formulations of the present invention delivered via an osmotic delivery device, such as a DUROS® device, include, but are not limited to the following. Increased treatment compliance can result in better efficacy and such increased compliance can be achieved using an implanted osmotic delivery device. Efficacy of treatment can be improved because an implantable osmotic device, such as a DUROS® device, can provide continuous and consistent delivery of drug (e.g., GLP-1 or exenatide) 24 hours per day to provide better control of blood glucose levels day and night. Further, it is believed that incretins and incretin mimetics may protect the beta cells in the pancreas and slow down the progression of type 2 diabetes mellitus. Twenty-four hour continuous and consistent drug delivery of incretins or incretin mimetics from the DUROS® device thus can provide even greater protection of the beta cells and may provide reversal of the disease progression. Continuous delivery of insulinotropic peptides (e.g., GLP-1 or exenatide) from the DUROS® device also allows treated subjects complete flexibility in planning meals and thus an increased quality of life compared to, for example, treatment with bolus injections that need to be timed relative to the major meals of the day. Also, unlike other sustained release formulations and depot injections, drug dosing when using a DUROS® device can be immediately halted by removal of the device, for example, if a safety issue arises for a particular subject.

In addition to GLP-1 derivatives and analogues demonstrating insulinotropic action, other derivatives of GLP-1 (e.g., GLP-1(9-36) amide) have been shown to reduce blood glucose by a mechanism that does not involve insulin secretion (Deacon, C. F., et al., Am. J. Physiol. Endocrinol. Metab. 282:E873-E879 (2002)). Further, GLP-1(9-36) amide has been shown to reduce postprandial glycemia independently of gastric emptying and insulin secretion (Meier, J. J., et al., Am. J. Physiol. Endocrinol. Metab. 290:E1118-E1123 (2006)). Accordingly, in another aspect, the present invention includes formulation of such GLP-1 derivatives into particles, suspension of the particles in a vehicle, and delivery of these suspension formulations to subjects to reduce blood glucose and/or to reduce postprandial glycemia essentially as described herein above for GLP-1 derivatives and analogues demonstrating insulinotropic action. In addition, GIP(3-42) appears to be a weak GIP receptor antagonist that does not exert insulin-related glucoregulation. Such GIP derivatives may also be formulated (singly or in combination with other peptides) following the guidance presented herein.

The present invention also includes methods of manufacturing the formulations of the present invention, including the particle formulations, suspension vehicles, and suspension formulations described herein above.

4.0.0 Suspension Formulation Uses

The suspension formulations as described herein provide promising alternatives to insulin therapy for subjects with diabetes mellitus. Diabetes mellitus type 2 or Type 2 Diabetes (also called non-insulin-dependent diabetes mellitus (NIDDM) or adult-onset diabetes) is a metabolic disorder that is primarily characterized by insulin resistance, relative insulin deficiency and hyperglycemia. The suspension formulations of the present invention, comprising insulinotropic peptides, are useful for stimulating insulin secretion, suppressing glucagon secretion, slowing gastric emptying, and possibly enhancing insulin sensitivity in peripheral tissues such as muscle and fat.

The suspension formulations of the present invention may be useful in the treatment of diabetes (e.g., diabetes mellitus, and gestational diabetes), and diabetic related disorders (e.g., diabetic cardiomyopathy, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia), as well as, hyperglycemia (e.g., related to treatment with medications that increase the risk of hyperglycemia, including beta blockers, thiazide diuretics, corticosteroids, niacin, pentamidine, protease inhibitors, L-asparaginase, and some antipsychotic agents), reducing food intake (e.g., treating obesity, controlling appetite, or reducing weight), stroke, lowering plasma lipids, acute coronary syndrome, hibernating myocardium, regulating gastrointestinal motility, and increasing urine flow.

In addition, the suspension formulations of the present invention may be potential regulators of appetite in subjects treated with the formulations.

In one embodiment, suspension formulations are administered using an osmotic delivery device as described above. Examples of target rates of delivery for suspension formulations of the present invention, comprising insulinotropic peptides, include, but are not limited to: suspension formulations comprising particle formulations comprising GLP-1 (e.g., GLP-1(7-36)amide), between about 20 µg/day and about 900 µg/day, preferably between about 100 µg/day and about 600 µg/day, for example, at about 480 µg/day; and suspension formulations comprising particle formulations comprising exenatide, between about 5 µg/day and about 320 µg/day, preferably between about 5 µg/day and about 160 µg/day, for example, at about 10 µg/day to about 20 µg/day. An exit sheer rate of the suspension formulation from the osmotic delivery device is determined such that the target daily target delivery rate of the insulinotropic peptide is reasonably achieved by substantially continuous, uniform delivery of the suspension formulation from the osmotic delivery device. Examples of exit sheer rates include, but are not limited to, about 1 to about $1\times10^{-7}$ reciprocal second, preferably about $4\times10^{-2}$ to about $6\times10^4$ reciprocal second, more preferably $5\times10^{-3}$ to $1\times10^{-3}$ reciprocal second.

A subject being treated with the suspension formulations of the present invention may also benefit from co-treatment with other agents (e.g., sulfonylureas, meglitinides (e.g., repaglinide, and nateglinide), metformin, and combinations of such agents), alpha glucosidase inhibitors, amylin (as well as synthetic analogues such as pramlintide), dipeptidyl peptidase IV (DPP-IV) inhibitors (e.g., sitagliptin and vildagliptin), and long/short acting insulins.

Use of oral dipeptidyl peptidase-IV (DPP-IV or DPP-4) inhibitors orally to prevent cleavage of GLP-1 may be particularly useful when the suspension formulation of the present invention comprises a GLP-1 variant that is cleavable by dipeptidyl peptidase-IV (see, e.g., U.S. Pat. No. 7,205,409).

Example 5 presents data demonstrating that delivery of a formulation comprising exenatide using the DUROS® device resulted in decreased glucose levels and weight loss in treated animals.

Other objects may be apparent to one of ordinary skill upon reviewing the following specification and claims.

5.0.0 EXAMPLES

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the specifications for content and purity required of pharmaceutical products.

Example 1

Exenatide Particle Formulations

This example describes making exenatide particle formulations.

A. Formulation 1

Exenatide (0.25 g) was dissolved in 50 mM sodium citrate buffer at pH 6.04. The solution was dialyzed with a formulation solution containing sodium citrate buffer, sucrose, and methionine. The formulated solution was then spray dried using Buchi 290 with 0.7 mm nozzle, outlet temperature of 75° C., atomization pressure of 100 Psi, solid content of 2%, and flow rate of 2.8 mL/min. The dry powder contained 21.5% of exenatide with 4.7% residual moisture and 0.228 g/ml density.

B. Formulations 2 and 3

Two additional formulations of exenatide were prepared essentially by the method just described. Following here in Table 3 is a summary of the weight percentages (wt %) of the components of the Formulations 1, 2 and 3.

TABLE 3

| Component | Particle Formulation 1 (wt %) | Particle Formulation 2 (wt %) | Particle Formulation 3 (wt %) |
|---|---|---|---|
| Exenatide | 21.5 | 11.2 | 50.0 |
| Sodium Citrate* | 63.6 | 74.7 | 28.4 |
| Citric Acid* | 7.1 | 9.1 | 3.6 |
| Sucrose | 3.9 | 2.5 | 9.0 |
| Methionine | 3.9 | 2.5 | 9.0 |

*Sodium Citrate/Citric Acid formed the citrate buffer for this particle formulation.

Example 2

GLP-1 Dry Powder

This example describes making an GLP-1(7-36)amide particle formulation. GLP-1(7-36)amide (1.5 g) was dissolved in 5 mM sodium citrate buffer at pH 4. The solution was dialyzed with a formulation solution containing sodium citrate buffer and methionine. The formulated solution was then spray dried using Buchi 290 with 0.7 mm nozzle, outlet temperature of 70° C., atomization pressure of 100 Psi, solid content of 1.5%, and flow rate of 5 mL/min. The dry powder contained 90% of GLP-1(7-36)amide.

Example 3

Exenatide Suspension Formulation

This example describes making suspension formulations comprising a suspension vehicle and an exenatide particle formulation.

A. Suspension Formulation of 20 wt % Exenatide Particles

An exenatide particle formulation was generated by spray-drying, and contained 20 wt % exenatide, 32 wt % sucrose, 16 wt % methionine and 32 wt % citrate buffer.

A suspension vehicle was formed by dissolving the polymer polyvinylpyrrolidone in the solvent benzyl benzoate at approximately a 50/50 ratio by weight. The vehicle viscosity was approximately 12,000 to 18,000 poise when measured at 33° C. Particles containing the peptide exenatide were dispersed throughout the vehicle at a concentration of 10% particles by weight.

B. Suspension Formulations of Particle Formulations 1, 2, and 3

A suspension vehicle was formed by dissolving the polymer polyvinylpyrrolidone K-17 (typically having an approximate average molecular weight range of 7,900-10,800) in the solvent benzyl benzoate heated to approximately 65° C. under a dry atmosphere and reduced pressure at approximately a 50/50 ratio by weight. The vehicle viscosity was approximately 12,000 to 18,000 poise when measured at 33° C. Particle formulations 1-3, described in Example 1, were dispersed throughout the vehicle at the concentrations (by weight percent) shown in Table 4.

TABLE 4

| Component | Suspension Formulation 1 (wt %) | Suspension Formulation 2 (wt %) | Suspension Formulation 3 (wt %) |
|---|---|---|---|
| Particle Formulation 1 | 21.40 | — | — |
| Particle Formulation 2 | — | 11.73 | — |
| Particle Formulation 3 | — | — | 10.05 |
| Polyvinylpyrrolidone | 39.30 | 44.13 | 44.98 |
| Benzyl Benzoate | 39.30 | 44.13 | 44.98 |

Example 4

GLP-1(7-36)Amide Formulation

This example describes making a suspension formulation comprising a suspension vehicle and an GLP-1(7-36)amide particle formulation. A GLP-1(7-36)amide particle formulation was generated by spray-drying, and contained 90 wt % GLP-1, 5 wt % methionine and 5 wt % citrate buffer.

A suspension vehicle containing the polymer polyvinylpyrrolidone was dissolved in the solvent benzyl benzoate at approximately a 50/50 ratio by weight. The vehicle viscosity was approximately 12,000 to 18,000 poise when measured at 33° C. Particles containing the peptide GLP-1 (7-36)amide were dispersed throughout the vehicle at a concentration of 33% particles by weight.

Example 5

Continuous Delivery of Exenatide Using the DUROS® Device Resulted in Decreased Glucose Levels and Weight Loss in Treated Animals The data in this Example demonstrated the effect of continuous and consistent delivery of an exenatide formulation from the DUROS® device on glucose levels and weight in the Zucker Diabetic Fatty (ZDF) rat model of type 2 diabetes.

The ZDF rat model has been previously described as an accurate model for Type 2 diabetes based on impaired glucose tolerance caused by the inherited obesity gene mutation which leads to insulin resistance (see, e.g., Clark, J., et al., *Proc. Soc. Exp. Biol. Med.* 173: 68-75 (1983); Peterson, R. G., et al., *ILAR News* 32: 16-19 (1990); Peterson, R. G., In *Frontiers in Diabetes Research. Lessons from Animal Diabetes III*, edited by E. Shafrir, pp. 456-458. London: Smith-Gordon (1990); Vrabec, J. T., *Otolaryngol Head Neck Surg* 118: 304-308 (1998); Sparks, J. D., et al., *Metabolism* 47: 1315-1324 (1998)).

The study design presented in Table 5 was used.

TABLE 5

| Group | Treatment (mcg*/day) | ZDF Rate Type | Number of Males |
|---|---|---|---|
| 1 | Control | Obese | 6 |
| 2 | 20 | Obese | 6 |
| 3 | 20 | Lean | 6 |

*micrograms

Rats (Group 2, obese, and Group 3, lean, n=6/group) in treatment groups were exposed to 20 mcg/day of exenatide (Suspension Formulation 2; Example 3, Table 4) continuously delivered using DUROS® devices for seven 24 hour periods (wherein the device was inserted on day 1 and removed on day 8), while placebo devices were inserted into rats in the control group (Group 1; n=6). The DUROS® devices were inserted subcutaneously into each of the animals.

Over the treatment period the following endpoints were evaluated. Clinical signs/Mortality were assessed at least once daily. Body weight was determined prior to implantation, daily during the observation period, and at termination. Blood glucose was determined as follows: fasted blood samples collected on Days −1 and 8; and un-fasted blood samples were taken three times each day (4-6 hours apart) Days −1 and 8, with two un-fasted blood samples taken on Days −1 and 8. Blood glucose was determined using a OneTouch Ultra® (Johnson & Johnson, New Brunswick N.J.) blood glucose meter. Glucose levels were measured three times per day. Quantitative HbA1c was determined for fasted blood samples collected on Days −1 and 8 using a DCA 2000 Plus Analyzer (GMI, Inc., Ramsey Minn.). Serial blood samples were obtained pre-Implant (0), at 12, 24, 36, 48, 72 hours and at Days 5 and 7 after implantation. These samples were centrifuged, the plasma harvested, and stored at −70° C. Necropsy included macroscopic examination performed on Day 8 of the observation period.

FIG. 2 presents the data obtained for group mean body weights (in grams). Decreased body weight was observed in both obese (FIG. 2; closed squares) and lean (FIG. 2; closed triangles) rats treated with exenatide by Day 4 (Obese: Day 1=329±15.2 g versus Day 4=296.2±14.2 g ($p<0.01$); and lean: Day 1=265.4±9.1 g versus Day 4=237.6±7.8 g ($p<0.01$)). Overall, there was a 10.7% weight loss in obese treated rats and a 15.1% weight loss in lean treated rats by Day 6. In contrast, obese rats with placebo devices (FIG. 2; closed diamonds) showed a slight increase (1.8%) in body weight by Day 6.

Figure 3:
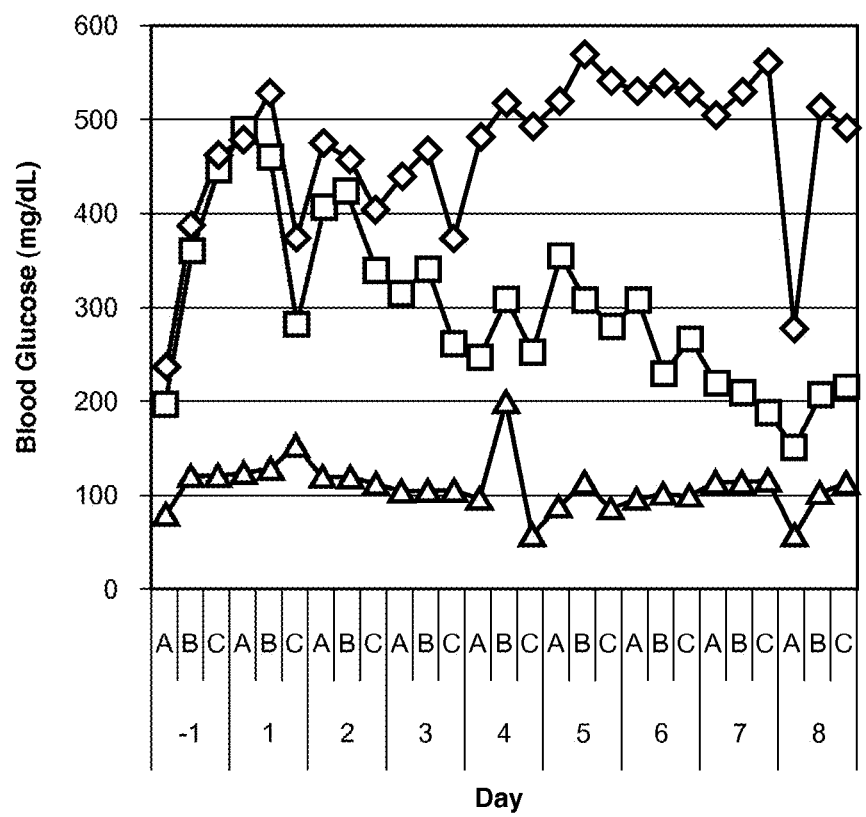
FIG. 3 presents data for group mean blood glucose concentrations of test animals treated by continuous delivery of exenatide from a DUROS® device. In the figure, the vertical axis is mean blood glucose in mg/dL (Blood Glucose (mg/dL)) and the horizontal axis is the day (Day), wherein each day has three associated blood glucose values (A, B, C). Day −1A is a fasting blood glucose value and Day 8A is a fasting blood glucose value. The obese animals of Group 1 (closed diamonds) were the control group to which 0 mcg of exenatide was administered per day. The animals of Group 2 (closed squares) were obese animals to which 20 mcg of exenatide from a DUROS® device was administered per day. The animals of Group 3 (closed triangles) were lean animals to which 20 mcg. of exenatide from a DUROS® device was administered per day.

FIG. 3 presents the data obtained for group mean blood glucose concentrations (in mg/dL). Decreased blood glucose levels were apparent in obese treated rats (FIG. 3; closed squares) compared to obese controls (FIG. 3; closed diamonds) within 1 day after DUROS® device insertion. Starting at Day 3 mean glucose levels in obese treated rats were 163±92 mg/dL, while obese control rats were 481±47 mg/dL ($p<0.05$). Between Days 3-7, obese rats treated with 20 mcg/day of exenatide had decreased blood glucose levels that approached those in lean animals, while placebo-treated obese rats had mean glucose levels of 502 mg/dL. Lean animals (FIG. 3; closed triangles) were consistently around glucose levels of 100 mg/dL. A glucose level of 100 mg/dL is considered to be normal.

Figure 4:
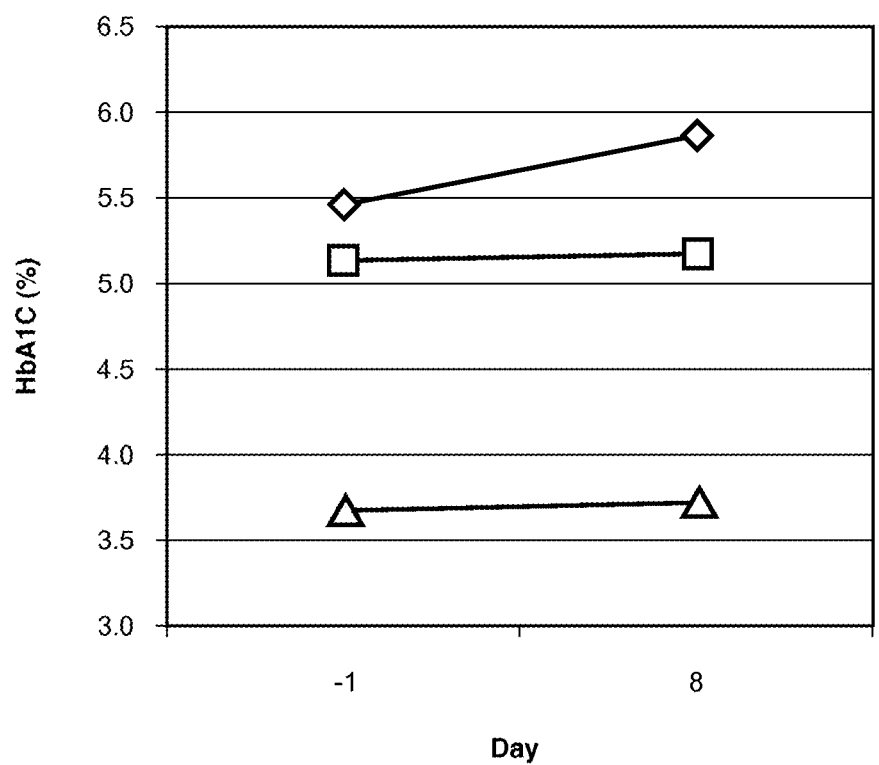
FIG. 4 presents data for group mean HbA1c values of test animals treated by continuous delivery of exenatide from a DUROS® device. In the figure, the vertical axis is mean percent HbA1c (HbA1c (%)) and the horizontal axis is the day (Day). The obese animals of Group 1 (closed diamonds) were the control group to which 0 mcg of exenatide was administered per day. The animals of Group 2 (closed squares) were obese animals to which 20 mcg of exenatide was administered per day. The animals of Group 3 (closed triangles) were lean animals to which 20 mcg of exenatide from a DUROS® device was administered per day.

FIG. 4 presents the data obtained for group mean blood HbA1c values. Treated obese rats (FIG. 4; closed squares) showed an overall increase of 5.8% in HbA1c levels, while obese control rats (FIG. 4; closed diamonds) showed an increase of 6.7% over the study period. Even though there was a decrease of mean blood glucose concentrations over time for the treated obese rats there did not appear to be a corresponding decrease in HbA1c in these animals. This result is likely because the study was not long enough as HbA1c levels are proportional to average blood glucose concentrations over one to two month periods.

These data demonstrated that continuous, uniform delivery of exenatide resulted in glucose-lowering together with a potent effect on body weight in treated animals. These results support the use of the DUROS® device for long-term steady state dosing of incretin mimetics, for example, a suspension formulation comprising exenatide, in the treatment of human diabetes.

As is apparent to one of skill in the art, various modification and variations of the above embodiments can be made without departing from the spirit and scope of this invention. Such modifications and variations are within the scope of this invention.

What is claimed is:

1. A suspension formulation comprising:
   a particle formulation comprising:
   an insulinotropic peptide, an antioxidant, and a buffer, wherein the insulinotropic peptide is at least one of exenatide, a derivative of exenatide, and an analogue of exenatide; and
   a non-aqueous, single-phase suspension vehicle that comprises about 20 wt % to about 60 wt % solvent and about 80 wt % to about 40 wt % pyrrolidone polymer, the suspension vehicle having a viscosity from 5,000 poise to 50,000 poise at 33° C.;
   wherein:
   the solvent is at least one of lauryl lactate, lauryl alcohol, and benzyl benzoate;
   30 to 90% by weight of the particle formulation is the insulinotropic peptide;
   the particle formulation has a wt % ratio of insulinotropic peptide to antioxidant of 2.5/1 to 10/1; and
   the particle formulation is dispersed in the suspension vehicle.

2. The suspension formulation of claim 1, wherein the insulinotropic peptide is exenatide.

3. The suspension formulation of claim 1, wherein the buffer is selected from at least one of citrate, histidine, succinate, and tris.

4. The suspension formulation of claim 3, wherein the buffer is citrate.

5. The suspension formulation of claim 1, wherein the antioxidant is methionine.

6. The suspension formulation of claim 1, wherein the solvent is benzyl benzoate.

7. The suspension formulation of claim 1, wherein the pyrrolidone polymer is polyvinylpyrrolidone.

8. The suspension formulation of claim 1, further comprising a carbohydrate.

9. The suspension formulation of claim 8, wherein the carbohydrate is at least one of lactose, sucrose, trehalose, cellobiose, and raffinose.

10. The suspension formulation of claim 9, wherein the carbohydrate is sucrose.

11. The suspension formulation of claim 10, wherein the particle formulation comprises exenatide, sucrose, methionine, and citrate.

12. The suspension formulation of claim 11, wherein the particle formulation has a wt % ratio of insulinotropic peptide to antioxidant of 5/1 to 10/1.

13. The suspension formulation of claim 12, wherein the solvent is benzyl benzoate.

14. The suspension formulation of claim 13, wherein the pyrrolidone polymer is polyvinylpyrrolidone.

15. The suspension formulation of claim 1, wherein the particle formulation has a moisture content of less than 5 wt %.

16. The suspension formulation of claim 1, wherein particles of the particle formulation have a diameter of about 3 μm to about 50 μm.

17. A delivery device comprising a suspension formulation, the suspension formulation comprising:
   a particle formulation comprising:
   an insulinotropic peptide, an antioxidant, and a buffer, wherein the insulinotropic peptide is at least one of exenatide, a derivative of exenatide, and an analogue of exenatide; and
   a non-aqueous, single-phase suspension vehicle that consists essentially of about 20 wt % to about 60 wt % solvent and about 80 wt % to about 40 wt % pyrrolidone polymer, the suspension vehicle having a viscosity from 5,000 poise to 50,000 poise at 33° C.;
   wherein:
   the solvent is at least one of lauryl lactate, lauryl alcohol, and benzyl benzoate;
   30 to 90% by weight of the particle formulation is the insulinotropic peptide;
   the particle formulation has a wt % ratio of insulinotropic peptide to antioxidant of 2.5/1 to 10/1; and
   the particle formulation is dispersed in the suspension vehicle.

18. The delivery device of claim 17, wherein the delivery device delivers the suspension formulation at least one of osmotically, mechanically, electromechanically, and chemically.

19. The delivery device of claim 17, wherein the insulinotropic peptide is exenatide.

20. The delivery device of claim 19, wherein the buffer is selected from at least one of citrate, histidine, succinate, and tris.

21. The delivery device of claim 19, wherein the buffer is citrate.

22. The delivery device of claim 19, wherein the antioxidant is methionine.

23. The delivery device of claim 19, wherein the suspension formulation further comprises a carbohydrate.

24. The delivery device of claim 23, wherein the carbohydrate is at least one of lactose, sucrose, trehalose, cellobiose, and raffinose.

25. The delivery device of claim 24, wherein the carbohydrate is sucrose.

26. The delivery device of claim 25, wherein the particle formulation comprises exenatide, sucrose, methionine, and citrate.

27. A method of treating type II diabetes in a subject in need of such treatment, the method comprising:
  delivering a suspension formulation from a delivery device at a substantially uniform rate for a period of about one month to about one year, the suspension formulation comprising:
    a particle formulation comprising:
      an insulinotropic peptide, an antioxidant, and a buffer, wherein the insulinotropic peptide is at least one of exenatide, a derivative of exenatide, and an analogue of exenatide; and
    a non-aqueous, single-phase suspension vehicle that consists essentially of about 20 wt % to about 60 wt % solvent and about 80 wt % to about 40 wt % pyrrolidone polymer, the suspension vehicle having a viscosity from 5,000 poise to 50,000 poise at 33° C.;
  wherein:
    the solvent is at least one of lauryl lactate, lauryl alcohol, and benzyl benzoate;
    30 to 90% by weight of the particle formulation is the insulinotropic peptide;
    the particle formulation has a wt % ratio of insulinotropic peptide to antioxidant of 2.5/1 to 10/1; and
    the particle formulation is dispersed in the suspension vehicle.

28. The method of claim 27, wherein the insulinotropic peptide is exenatide.

29. A method for the reduction of at least one of body weight in a subject, glucose concentrations in blood of the subject, and HbA1C levels in the subject, the method comprising:
  delivering a suspension formulation from a delivery device at a substantially uniform rate for a period of about one month to about one year, the suspension formulation comprising:
    a particle formulation comprising:
      an insulinotropic peptide, an antioxidant, and a buffer, wherein the insulinotropic peptide is at least one of exenatide, a derivative of exenatide, and an analogue of exenatide; and
    a non-aqueous, single-phase suspension vehicle that consists essentially of about 20 wt % to about 60 wt % solvent and about 80 wt % to about 40 wt % pyrrolidone polymer, the suspension vehicle having a viscosity from 5,000 poise to 50,000 poise at 33° C.;
  wherein:
    the solvent is at least one of lauryl lactate, lauryl alcohol, and benzyl benzoate;
    30 to 90% by weight of the particle formulation is the insulinotropic peptide;
    the particle formulation has a wt % ratio of insulinotropic peptide to antioxidant of 2.5/1 to 10/1; and
    the particle formulation is dispersed in the suspension vehicle.

30. The method of claim 29, wherein the insulinotropic peptide is exenatide.

* * * * *